US011506628B2

(12) United States Patent
    Watanabe et al.

(10) Patent No.: US 11,506,628 B2
(45) Date of Patent: Nov. 22, 2022

(54) SENSOR ELEMENT

(71) Applicant: NGK INSULATORS, LTD., Nagoya (JP)

(72) Inventors: Yusuke Watanabe, Nagoya (JP); Shiho Iwai, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 185 days.

(21) Appl. No.: 16/996,032

(22) Filed: Aug. 18, 2020

(65) Prior Publication Data

US 2021/0063344 A1    Mar. 4, 2021

(30) Foreign Application Priority Data

Aug. 28, 2019  (JP) .............................. JP2019-155232

(51) Int. Cl.
    *G01N 27/407*    (2006.01)
    *G01N 27/41*     (2006.01)
    *G01N 33/00*     (2006.01)

(52) U.S. Cl.
    CPC ..... *G01N 27/4075* (2013.01); *G01N 27/4071* (2013.01); *G01N 27/41* (2013.01); *G01N 33/0037* (2013.01)

(58) Field of Classification Search
    CPC ........... G01N 27/4075; G01N 27/4071; G01N 27/41; G01N 33/0037; G01N 27/4074; G01N 27/4067; G01N 27/4162; G01N 27/419; G01N 27/406–41; G01N 33/0004–0075; Y02A 50/20
    See application file for complete search history.

(56) References Cited

U.S. PATENT DOCUMENTS

| | | | | |
|---|---|---|---|---|
| 5,763,763 A | * | 6/1998 | Kato | G01N 27/419 73/31.06 |
| 5,893,968 A | * | 4/1999 | Kato | G01N 27/419 73/23.31 |
| 2009/0242402 A1 | * | 10/2009 | Horisaka | G01N 33/0037 204/412 |
| 2016/0223487 A1 | * | 8/2016 | Okamoto | G01N 27/4074 |

FOREIGN PATENT DOCUMENTS

| | | | |
|---|---|---|---|
| EP | 859233 B1 | * 10/2008 | ......... G01N 27/4074 |
| JP | 3050781 B2 | 6/2000 | |
| JP | 2014-190940 A | 10/2014 | |
| JP | 2014-209128 A | 11/2014 | |
| JP | 6292735 B2 | 3/2018 | |

* cited by examiner

Primary Examiner — Joshua L Allen
(74) Attorney, Agent, or Firm — Mattingly & Malur, PC

(57) ABSTRACT

In a sensor element for a limiting-current type gas sensor measuring concentration of NOx in a measurement gas, an inner pump electrode located to face a first internal space communicating, under predetermined diffusion resistance, with a gas inlet through which a measurement gas is introduced from an external space is made of a cermet of a Pt—Au alloy and zirconia, and includes a first portion located on a surface farther from a heater part and a second portion located on a surface closer to the heater part from among surfaces opposing each other in the first internal space, an Au content with respect to the Pt—Au alloy as a whole of the second portion is 0.3 wt % or more smaller than that of the first portion, and a total area of the first portion and the second portion is 10 $mm^2$ to 25 $mm^2$.

4 Claims, 5 Drawing Sheets

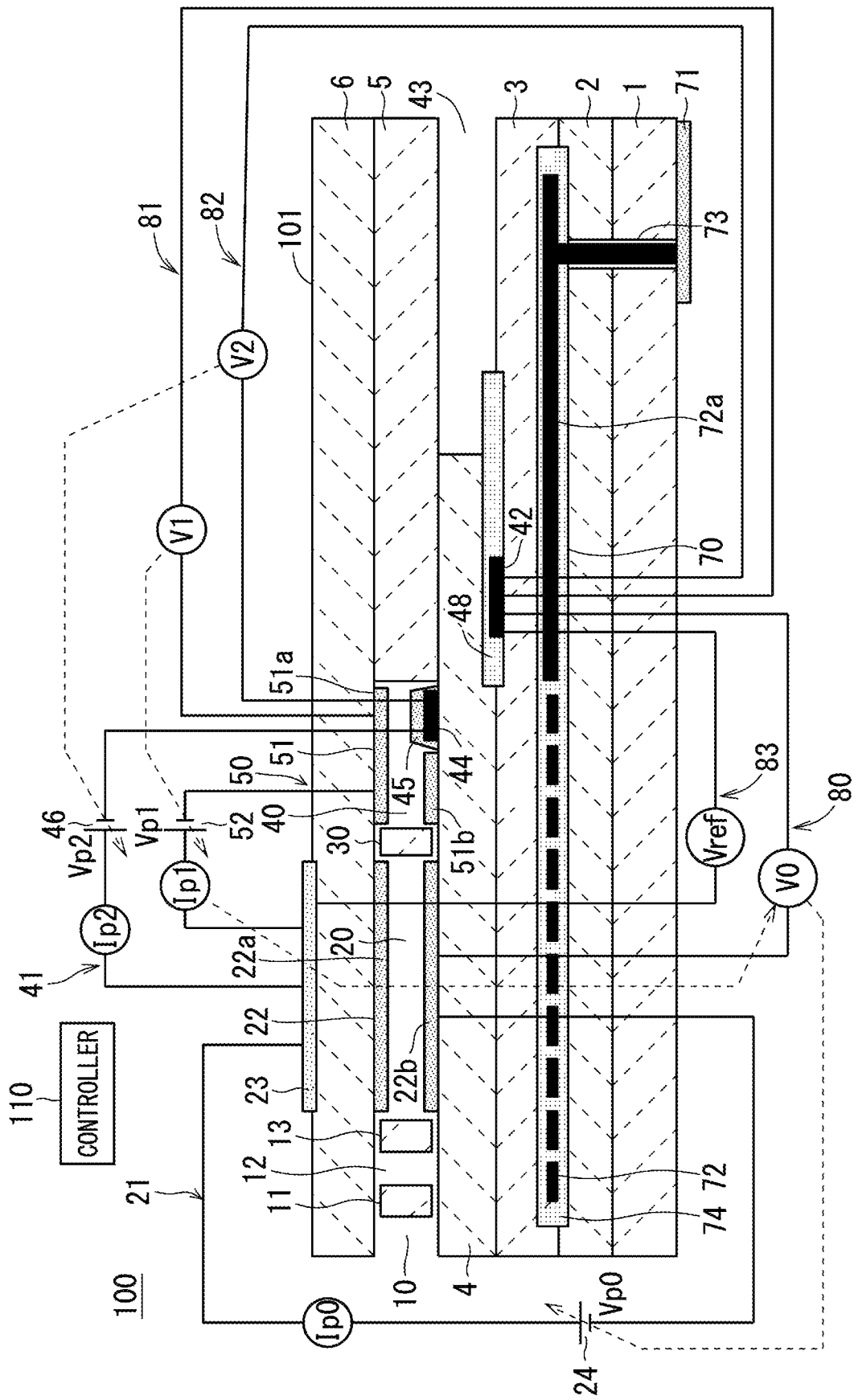
F I G. 1

F I G. 5
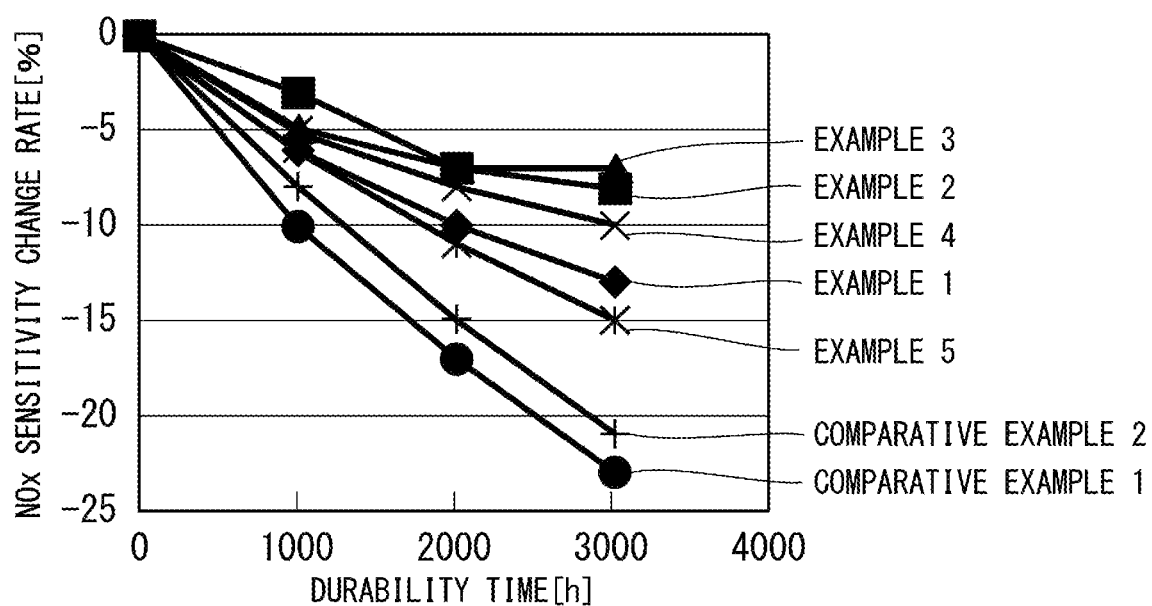

SENSOR ELEMENT

CROSS-REFERENCE TO RELATED APPLICATION

The present application claims priority from Japanese application JP2019-155232, filed on Aug. 28, 2019, the contents of which is hereby incorporated by reference into this application.

BACKGROUND OF THE INVENTION

Field of the Invention

The present invention relates to a gas sensor for determining concentration of nitrogen oxides (NOx), and, in particular, to an electrode of a sensor element thereof.

Description of the Background Art

A limiting-current type gas sensor (NOx sensor) including a sensor element containing an oxygen-ion conductive solid electrolyte as a main component has already been known (see, for example, Japanese Patent No. 3050781). In determining a NOx concentration using such a gas sensor, a measurement gas is first introduced into a space (an internal space) inside the sensor element under predetermined diffusion resistance, and oxygen in the measurement gas is pumped out by an electrochemical pump cell, for example, referred to as a main pump cell and an auxiliary pump cell (a first electrochemical pump cell and a second electrochemical pump cell in Japanese Patent No. 3050781) to sufficiently reduce an oxygen concentration of the measurement gas in advance. NOx in the measurement gas is then reduced or decomposed by a measurement electrode (third inner pump electrode in Japanese Patent No. 3050781) functioning as a reduction catalyst, and oxygen thus generated is pumped out by an electrochemical pump cell (a third electrochemical pump cell in Japanese Patent No. 3050781) different from the above-mentioned electrochemical pump cell, including the measurement electrode, and, for example, referred to as a measurement pump cell. The NOx concentration is determined using a constant functional relationship between a current (NOx current) flowing through the measurement pump cell and the NOx concentration.

In the gas sensor (NOx sensor), use of Pt to which Au has been added (an Au—Pt alloy) as a metal component of an inner pump electrode located in the internal space and forming the main pump cell to suppress decomposition of NOx caused when the main pump cell pumps out oxygen from the internal space and to enhance NOx detection accuracy has already been known (see, for example, Japanese Patent Application Laid-Open No. 2014-190940 and Japanese Patent Application Laid-Open No. 2014-209128).

A gas sensor that can determine the NOx concentration by, after sufficiently reducing the oxygen concentration of the measurement gas using the pump cell as in the above-mentioned case, calculating total concentration of oxygen and NOx based on an oxygen-ion current generated through decomposition of oxygen and NOx in the measurement gas using a sensor cell while calculating concentration of only oxygen based on oxygen ions generated through decomposition of only oxygen in the measurement gas using a monitor cell, and subtracting the latter from the former has also already been known (see, for example, Japanese Patent No. 6292735). In the gas sensor disclosed in Japanese Patent No. 6292735, the electrode of the pump cell is made of the alloy of Pt and Au.

A gas sensor as disclosed in Japanese Patent No. 3050781, Japanese Patent Application Laid-Open No. 2014-190940, Japanese Patent Application Laid-Open No. 2014-209128, and Japanese Patent No. 6292735 is used in a state of being heated to a high temperature to activate a solid electrolyte, so that, if the measurement gas having a high oxygen concentration continues to be introduced into the internal space, $PtO_2$ generated through oxidation of Pt in the pump electrode located in the space may evaporate (transpire), and, furthermore, Au might evaporate (transpire) together. Such evaporation of Au causes a problem in that NOx is decomposed before the measurement gas reaches the measurement electrode (Japanese Patent No. 3050781) and a sensor electrode of the sensor cell (Japanese Patent No. 6292735) to deteriorate measurement accuracy (measurement sensitivity). Attachment of evaporating Au to the measurement electrode and the sensor electrode causes deterioration of the measurement accuracy and deterioration of responsiveness.

Japanese Patent No. 6292735 discloses an Au adsorption layer located to oppose the pump electrode in the internal space, in particular, to prevent the latter problem.

The configuration, however, does not have an effect of suppressing evaporation of Au from the pump electrode. It is also necessary to secure a space for the Au adsorption layer, which does not contribute to pumping of oxygen.

SUMMARY

The present invention relates to a gas sensor for determining concentration of nitrogen oxides (NOx), and is, in particular, directed to a configuration of an electrode of a sensor element thereof.

According to the present invention, a sensor element for a limiting-current type gas sensor measuring concentration of NOx in a measurement gas includes: a base part made of an oxygen-ion conductive solid electrolyte; a gas inlet through which the measurement gas is introduced from an external space; a first internal space communicating with the gas inlet under predetermined diffusion resistance; a main pump cell as an electrochemical pump cell including an inner pump electrode located to face the first internal space, an out-of-space pump electrode located to face a space other than the first internal space, and the solid electrolyte located between the inner pump electrode and the out-of-space pump electrode; a measurement electrode located inside the sensor element, at least one diffusion control part being located between the measurement electrode and the first internal space; a reference electrode located inside the sensor element and capable of being in contact with a reference gas; a measurement pump cell as an electrochemical pump cell including the measurement electrode, the out-of-space pump electrode, and the solid electrolyte located between the measurement electrode and the out-of-space pump electrode; and a heater part buried in the sensor element and heating the sensor element, wherein the inner pump electrode is at least made of a cermet of a Pt—Au alloy and zirconia, and includes: a first portion located on a surface farther from the heater part from among surfaces opposing each other in the first internal space; and a second portion located on a surface closer to the heater part from among the surfaces opposing each other in the first internal space, an Au content with respect to the Pt—Au alloy as a whole of the second portion is 0.3 wt % or more smaller than an Au content with respect to the Pt—Au alloy as a whole of the first portion, and a total area of the first portion and the second portion is 10 mm² to 25 mm².

Accordingly, the influence of evaporation of Au from the inner pump electrode caused by continuous use on NOx measurement accuracy of the gas sensor is suppressed. Furthermore, decomposition of NOx in the internal space caused in a case where an oxygen concentration is high is suppressed.

It is thus an object of the present invention to provide a gas sensor in which the influence of evaporation of Au from an inner pump electrode on measurement accuracy is suppressed.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 schematically shows one example of a configuration of a gas sensor 100 including a vertical sectional view taken along a longitudinal direction of a sensor element 101;

FIG. 5 is a plot of NOx sensitivity change rates of gas sensors of Examples 1 to 5 and Comparative Examples 1 and 2 against elapsed times of an accelerated durability test.

DESCRIPTION OF THE PREFERRED EMBODIMENTS

<General Configuration of Gas Sensor>

Figure 2:
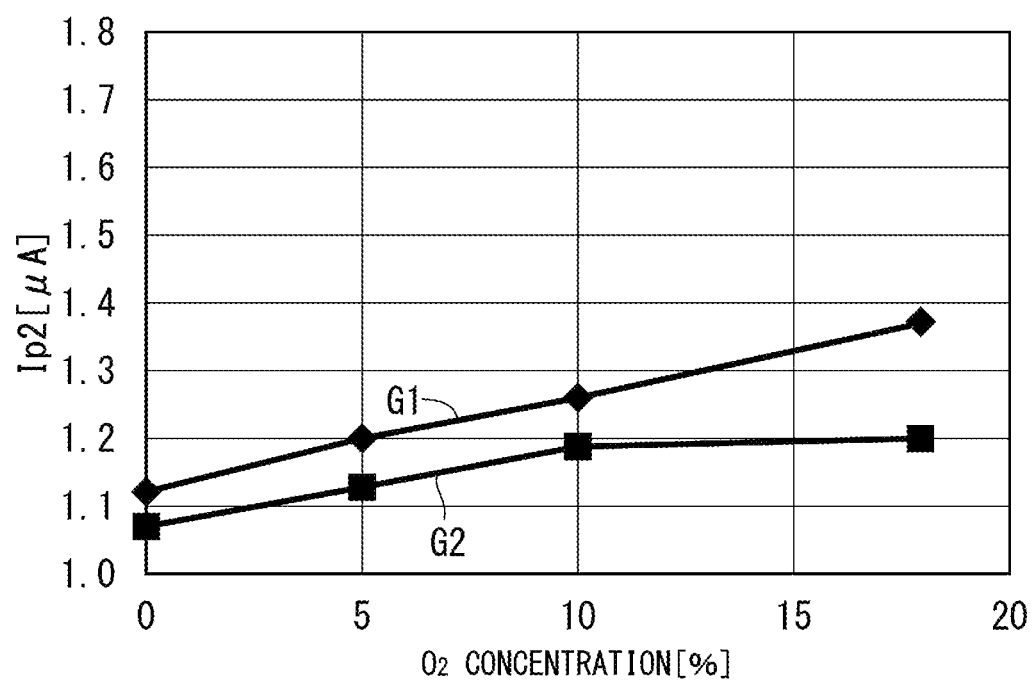
FIG. 2 is a plot of NOx currents Ip2 obtained through model gas measurement using two gas sensors 100 in different states against oxygen concentrations of model gases.

A general configuration of a gas sensor 100 including a sensor element 101 according to the present embodiment will be described first. In the present embodiment, the gas sensor 100 is a limiting-current type NOx sensor to sense NOx and measure concentration thereof using the sensor element 101. The gas sensor 100 further includes a controller 110 to control operation of each part and identify the NOx concentration based on a NOx current flowing through the sensor element 101.

FIG. 1 schematically shows one example of a configuration of the gas sensor 100 including a vertical sectional view taken along a longitudinal direction of the sensor element 101.

The sensor element 101 is a planar (elongated planar) element having a structure in which six solid electrolyte layers, namely, a first substrate layer 1, a second substrate layer 2, a third substrate layer 3, a first solid electrolyte layer 4, a spacer layer 5, and a second solid electrolyte layer 6 each made of zirconia ($ZrO_2$) (e.g., yttrium stabilized zirconia (YSZ)) as an oxygen-ion conductive solid electrolyte are laminated in the stated order from a bottom side of FIG. 1. The solid electrolyte forming these six layers is dense and airtight. A surface on an upper side and a surface on a lower side of each of these six layers in FIG. 1 are hereinafter also simply referred to as an upper surface and a lower surface, respectively. A part of the sensor element 101 made of the solid electrolyte as a whole is generically referred to as a base part.

The sensor element 101 is manufactured, for example, by performing predetermined processing, printing of circuit patterns, and the like on ceramic green sheets corresponding to the respective layers, then laminating them, and further firing them for integration.

Between a lower surface of the second solid electrolyte layer 6 and an upper surface of the first solid electrolyte layer 4 in one leading end portion of the sensor element 101, a gas inlet 10, a first diffusion control part 11, a buffer space 12, a second diffusion control part 13, a first internal space 20, a third diffusion control part 30, and a second internal space 40 are formed adjacent to each other to communicate in the stated order.

The gas inlet 10, the buffer space 12, the first internal space 20, and the second internal space 40 are spaces inside the sensor element 101 looking as if they were provided by hollowing out the spacer layer 5, and having an upper portion, a lower portion, and a side portion respectively defined by the lower surface of the second solid electrolyte layer 6, the upper surface of the first solid electrolyte layer 4, and a side surface of the spacer layer 5.

The first diffusion control part 11, the second diffusion control part 13, and the third diffusion control part 30 are each provided as two horizontally long slits (whose openings have longitudinal directions perpendicular to the page of FIG. 1). A part extending from the gas inlet 10 to the second internal space 40 is also referred to as a gas distribution part.

At a location farther from the leading end than the gas distribution part is, a reference gas introduction space 43 having a side portion defined by a side surface of the first solid electrolyte layer 4 is provided between an upper surface of the third substrate layer 3 and a lower surface of the spacer layer 5. For example, air is introduced into the reference gas introduction space 43 as a reference gas when the NOx concentration is measured.

An air introduction layer 48 is a layer made of porous alumina, and the reference gas is introduced into the air introduction layer 48 through the reference gas introduction space 43. The air introduction layer 48 is formed to cover a reference electrode 42.

The reference electrode 42 is an electrode formed to be sandwiched between the upper surface of the third substrate layer 3 and the first solid electrolyte layer 4, and the air introduction layer 48 leading to the reference gas introduction space 43 is provided around the reference electrode 42 as described above. As will be described below, an oxygen concentration (oxygen partial pressure) in the first internal space 20 and the second internal space 40 can be measured using the reference electrode 42.

In the gas distribution part, the gas inlet 10 is a part opening to an external space, and a measurement gas is taken from the external space into the sensor element 101 through the gas inlet 10.

The first diffusion control part 11 is a part providing predetermined diffusion resistance to the measurement gas taken through the gas inlet 10.

The buffer space 12 is a space provided to guide the measurement gas introduced from the first diffusion control part 11 to the second diffusion control part 13.

The second diffusion control part 13 is a part providing predetermined diffusion resistance to the measurement gas introduced from the buffer space 12 into the first internal space 20.

In introducing the measurement gas from outside the sensor element 101 into the first internal space 20, the measurement gas having abruptly been taken into the sensor element 101 through the gas inlet 10 due to pressure fluctuations (pulsation of exhaust pressure in a case where the measurement gas is an exhaust gas of a vehicle) of the measurement gas in the external space is not directly introduced into the first internal space 20 but is introduced into the first internal space 20 after concentration fluctuations of the measurement gas are canceled through the first diffusion control part 11, the buffer space 12, and the second diffusion control part 13. This makes the concentration fluctuations of the measurement gas introduced into the first internal space 20 almost negligible.

The first internal space 20 is provided as a space to adjust oxygen partial pressure of the measurement gas introduced through the second diffusion control part 13. The oxygen partial pressure is adjusted by operating a main pump cell 21.

The main pump cell 21 is an electrochemical pump cell including an inner pump electrode 22, an outer (out-of-space) pump electrode 23, and the second solid electrolyte layer 6 sandwiched between these electrodes. The inner pump electrode 22 has a ceiling electrode portion 22a provided on substantially the entire lower surface of a portion of the second solid electrolyte layer 6 facing the first internal space 20, and the outer pump electrode 23 is provided in a region, on an upper surface of the second solid electrolyte layer 6 (one main surface of the sensor element 101), corresponding to the ceiling electrode portion 22a to be exposed to the external space.

The inner pump electrode 22 is formed on upper and lower solid electrolyte layers (the second solid electrolyte layer 6 and the first solid electrolyte layer 4) defining the first internal space 20. Specifically, the ceiling electrode portion 22a (a first portion) is formed on the lower surface of the second solid electrolyte layer 6, which provides a ceiling surface to the first internal space 20, and a bottom electrode portion 22b (a second portion) is formed on the upper surface of the first solid electrolyte layer 4, which provides a bottom surface to the first internal space 20. The ceiling electrode portion 22a and the bottom electrode portion 22b are connected by a conducting portion (not illustrated) provided on a side wall surface (an inner surface) of the spacer layer 5 forming opposite side wall portions of the first internal space 20. The ceiling electrode portion 22a and the bottom electrode portion 22b are provided to be rectangular in plan view.

The inner pump electrode 22 is formed using a material having a weakened reducing ability with respect to a NOx component in the measurement gas. Specifically, the inner pump electrode 22 is formed as a porous cermet electrode of an Au—Pt alloy and $ZrO_2$. Containing (addition) of Au has an effect of weakening the reducing ability with respect to the NOx component. Details of the inner pump electrode 22 will be described below.

On the other hand, the outer pump electrode 23 is formed, for example, as a porous cermet electrode of Pt or an alloy thereof and $ZrO_2$ to be rectangular in plan view.

The main pump cell 21 can pump out oxygen in the first internal space 20 to the external space or pump in oxygen in the external space to the first internal space 20 by applying, from a variable power supply 24, a desired pump voltage Vp0 between the inner pump electrode 22 and the outer pump electrode 23 to allow a main pump current Ip0 to flow between the inner pump electrode 22 and the outer pump electrode 23 in a positive or negative direction. The pump voltage Vp0 applied between the inner pump electrode 22 and the outer pump electrode 23 by the main pump cell 21 is also referred to as a main pump voltage Vp0.

To detect the oxygen concentration (oxygen partial pressure) in an atmosphere in the first internal space 20, the inner pump electrode 22, the second solid electrolyte layer 6, the spacer layer 5, the first solid electrolyte layer 4, the third substrate layer 3, and the reference electrode 42 constitute a main sensor cell 80 as an electrochemical sensor cell.

The oxygen concentration (oxygen partial pressure) in the first internal space 20 can be known by measuring electromotive force V0 in the main sensor cell 80.

Furthermore, the controller 110 performs feedback control of the main pump voltage Vp0 so that the electromotive force V0 is constant, thereby to control the main pump current Ip0. The oxygen concentration in the first internal space 20 is thereby maintained to have a predetermined constant value.

The third diffusion control part 30 is a part providing predetermined diffusion resistance to the measurement gas having an oxygen concentration (oxygen partial pressure) controlled by operation of the main pump cell 21 in the first internal space 20, and guiding the measurement gas to the second internal space 40.

The second internal space 40 is provided as a space to perform processing concerning measurement of the nitrogen oxide (NOx) concentration of the measurement gas introduced through the third diffusion control part 30. The NOx concentration is measured, mainly in the second internal space 40 in which the oxygen concentration has been adjusted by an auxiliary pump cell 50, further by operation of a measurement pump cell 41.

After the oxygen concentration (oxygen partial pressure) is adjusted in advance in the first internal space 20, the auxiliary pump cell 50 further adjusts the oxygen partial pressure of the measurement gas introduced through the third diffusion control part 30 in the second internal space 40. The oxygen concentration in the second internal space 40 can thereby be maintained constant with high accuracy, and thus the NOx concentration can be measured with high accuracy in the gas sensor 100.

The auxiliary pump cell 50 is an auxiliary electrochemical pump cell including an auxiliary pump electrode 51, the outer pump electrode 23 (not limited to the outer pump electrode 23 and only required to be any appropriate electrode outside the sensor element 101), and the second solid electrolyte layer 6. The auxiliary pump electrode 51 has a ceiling electrode portion 51a provided on substantially the entire lower surface of a portion of the second solid electrolyte layer 6 facing the second internal space 40.

The auxiliary pump electrode 51 is provided in the second internal space 40 in a similar form to the inner pump electrode 22 provided in the first internal space 20 described previously. That is to say, the ceiling electrode portion 51a is formed on the second solid electrolyte layer 6, which provides a ceiling surface to the second internal space 40, and a bottom electrode portion 51b is formed on the first solid electrolyte layer 4, which provides a bottom surface to the second internal space 40. The ceiling electrode portion 51a and the bottom electrode portion 51b are rectangular in plan view, and are connected by a conducting portion (not illustrated) provided on the side wall surface (inner surface) of the spacer layer 5 forming opposite side wall portions of the second internal space 40.

As with the inner pump electrode 22, the auxiliary pump electrode 51 is formed using a material having a weakened reducing ability with respect to the NOx component in the measurement gas. The auxiliary pump electrode 51 is formed, for example, as a cermet electrode of an Au—Pt alloy containing Au of approximately 0.6 wt % to 1.4 wt % and $ZrO_2$ to have a porosity of 5% to 40% and a thickness of 5 μm to 20 μm. The Au—Pt alloy and $ZrO_2$ are only required to have a weight ratio $Pt:ZrO_2$ of approximately 7.0:3.0 to 5.0:5.0.

The auxiliary pump cell 50 can pump out oxygen in an atmosphere in the second internal space 40 to the external space or pump in oxygen in the external space to the second internal space 40 by applying a desired voltage Vp1 between the auxiliary pump electrode 51 and the outer pump electrode 23 under control performed by the controller 110.

To control the oxygen partial pressure in the atmosphere in the second internal space 40, the auxiliary pump electrode 51, the reference electrode 42, the second solid electrolyte layer 6, the spacer layer 5, the first solid electrolyte layer 4, and the third substrate layer 3 constitute an auxiliary sensor cell 81 as an electrochemical sensor cell.

The auxiliary pump cell 50 performs pumping using a variable power supply 52 whose voltage is controlled based on electromotive force V1 detected in the auxiliary sensor cell 81 in accordance with the oxygen partial pressure in the second internal space 40. The oxygen partial pressure in the atmosphere in the second internal space 40 is thereby controlled to a low partial pressure having substantially no effect on measurement of NOx.

At the same time, a resulting auxiliary pump current Ip1 is used to control the electromotive force in the main sensor cell 80. Specifically, the auxiliary pump current Ip1 is input, as a control signal, into the main sensor cell 80, and, through control of the electromotive force V0 therein, the oxygen partial pressure of the measurement gas introduced through the third diffusion control part 30 into the second internal space 40 is controlled to have a gradient that is always constant. In use as the NOx sensor, the oxygen concentration in the second internal space 40 is maintained to have a constant value of approximately 0.001 ppm by the action of the main pump cell 21 and the auxiliary pump cell 50.

The measurement pump cell 41 measures the NOx concentration of the measurement gas in the second internal space 40. The measurement pump cell 41 is an electrochemical pump cell including a measurement electrode 44, the outer pump electrode 23, the second solid electrolyte layer 6, the spacer layer 5, and the first solid electrolyte layer 4. The measurement electrode 44 is provided on an upper surface of a portion of the first solid electrolyte layer 4 facing the second internal space 40 to be separated from the third diffusion control part 30.

The measurement electrode 44 is a porous cermet electrode. The measurement electrode 44 is formed, for example, as a cermet electrode of Pt or an alloy thereof and $ZrO_2$. The measurement electrode 44 also functions as a NOx reduction catalyst to reduce NOx existing in the atmosphere in the second internal space 40. Furthermore, the measurement electrode 44 is covered with a fourth diffusion control part 45.

The fourth diffusion control part 45 is a film formed of a porous body containing alumina ($Al_2O_3$) as a main component. The fourth diffusion control part 45 plays a role in limiting the amount of NOx flowing into the measurement electrode 44, and also functions as a protective film of the measurement electrode 44.

The measurement pump cell 41 can pump out oxygen generated through decomposition of NOx in an atmosphere around the measurement electrode 44, and detect the amount of generated oxygen as a pump current Ip2 under control performed by the controller 110.

To detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute a measurement sensor cell 82 as an electrochemical sensor cell. A variable power supply 46 is controlled based on electromotive force V2 detected in the measurement sensor cell 82 in accordance with the oxygen partial pressure around the measurement electrode 44.

The measurement gas introduced into the second internal space 40 is to reach the measurement electrode 44 through the fourth diffusion control part 45 under a situation in which the oxygen partial pressure is controlled. NOx in the measurement gas around the measurement electrode 44 is reduced ($2NO \rightarrow N_2+O_2$) to generate oxygen. Oxygen as generated is to be pumped by the measurement pump cell 41, and, at this time, a voltage Vp2 of the variable power supply 46 is controlled so that the electromotive force V2 detected in the measurement sensor cell 82 is constant. The amount of oxygen generated around the measurement electrode 44 is proportional to the NOx concentration of the measurement gas, and thus the NOx concentration of the measurement gas is to be calculated using the pump current Ip2 in the measurement pump cell 41. The pump current Ip2 is hereinafter also referred to as a NOx current Ip2.

If the measurement electrode 44, the first solid electrolyte layer 4, the third substrate layer 3, and the reference electrode 42 are combined to constitute an oxygen partial pressure detection means as an electrochemical sensor cell, electromotive force can be detected in accordance with a difference between the amount of oxygen generated through reduction of a NOx component in the atmosphere around the measurement electrode 44 and the amount of oxygen contained in reference air, and the concentration of the NOx component in the measurement gas can thereby be determined.

The second solid electrolyte layer 6, the spacer layer 5, the first solid electrolyte layer 4, the third substrate layer 3, the outer pump electrode 23, and the reference electrode 42 constitute an electrochemical sensor cell 83, and oxygen partial pressure of the measurement gas outside the sensor can be detected using electromotive force Vref obtained by the sensor cell 83.

The sensor element 101 further includes a heater part 70 playing a role in temperature adjustment of heating the sensor element 101 and maintaining the temperature thereof to enhance oxygen ion conductivity of the solid electrolyte forming the base part.

The heater part 70 mainly includes a heater electrode 71, a heater element 72, a heater lead 72a, a through hole 73, and a heater insulating layer 74. A portion of the heater part 70 other than the heater electrode 71 is buried in the base part of the sensor element 101.

The heater electrode 71 is an electrode formed to be in contact with a lower surface of the first substrate layer 1 (the other main surface of the sensor element 101).

The heater element 72 is a resistive heating element provided between the second substrate layer 2 and the third substrate layer 3. The heater element 72 generates heat by being powered from a heater power supply, which is not illustrated in FIG. 1, outside the sensor element 101 through the heater electrode 71, the through hole 73, and the heater lead 72a, which constitute a current-carrying path. The heater element 72 is made of Pt, or contains Pt as a main component. The heater element 72 is buried, in a predetermined range of the sensor element 101 in which the gas distribution part is provided, to oppose the gas distribution part along the thickness of the element. The heater element 72 is provided to have a thickness of approximately 10 μm to 20 μm.

In the sensor element 101, each part of the sensor element 101 can be heated to a predetermined temperature and the temperature is maintained by allowing a current to flow through the heater electrode 71 to the heater element 72 to thereby cause the heater element 72 to generate heat. Specifically, the sensor element 101 is heated so that the solid electrolyte and the electrodes in the vicinity of the gas distribution part are at a temperature of approximately 700° C. to 900° C. The oxygen ion conductivity of the solid electrolyte forming the base part in the sensor element 101 is enhanced by the heating. A heating temperature of the heater element 72 when the gas sensor 100 is in use (when the sensor element 101 is driven) is referred to as a sensor element driving temperature.

In the gas sensor 100 having a configuration as described above, oxygen contained in the measurement gas is pumped out by operating the main pump cell 21 and further the auxiliary pump cell 50, and the measurement gas having oxygen partial pressure sufficiently reduced to a degree (e.g., 0.0001 ppm to 1 ppm) having substantially no effect on measurement of NOx reaches the measurement electrode 44. NOx in the measurement gas having reached the measurement electrode 44 is reduced to generate oxygen. Oxygen as generated is pumped out by the measurement pump cell 41, and the NOx current Ip2 flowing at the pumping out and the concentration of NOx in the measurement gas have a constant functional relationship (hereinafter, referred to as sensitivity characteristics).

The sensitivity characteristics are identified in advance using a plurality of types of model gases having known NOx concentrations prior to actual use of the gas sensor 100, and data thereof is stored in the controller 110. In actual use of the gas sensor 100, a signal representing a value of the NOx current Ip2 flowing in accordance with the NOx concentration of the measurement gas is momentarily provided to the controller 110, and the controller 110 successively calculates and outputs NOx concentrations based on the value and the identified sensitivity characteristics. The NOx concentration of the measurement gas can thereby be known in almost real time using the gas sensor 100.

<Details of Inner Pump Electrode>

The inner pump electrode 22 provided to face the first internal space 20 will be described in more detail next.

As described above, the inner pump electrode 22 includes the ceiling electrode portion 22a and the bottom electrode portion 22b. The ceiling electrode portion 22a and the bottom electrode portion 22b are made of a cermet of the Au—Pt alloy and $ZrO_2$, and provided to oppose each other along the thickness direction of the sensor element 101 each to be rectangular in plan view and to have a thickness of approximately 5 μm to 20 μm. The Au—Pt alloy and $ZrO_2$ are only required to have a weight ratio Pt:$ZrO_2$ of approximately 7.0:3.0 to 5.0:5.0.

On the other hand, the ceiling electrode portion 22a and the bottom electrode portion 22b are provided to satisfy the following requirements (a) to (c):

(a) The bottom electrode portion 22b has a smaller Au content than the ceiling electrode portion 22a;

(b) A difference (in content) between them is 0.3 wt % or more; and (c) A total area of them is 10 $mm^2$ to 25 $mm^2$.

The inner pump electrode 22 is required to contain Au to suppress decomposition of NOx when the main pump cell 21 pumps oxygen, while, once the sensor element 101 is heated by the heater part 70 when the gas sensor 100 is in use, Au might evaporate from the inner pump electrode 22, and is attached to the measurement electrode 44 or the fourth diffusion control part 45 on the measurement electrode 44, thereby to reduce NOx measurement accuracy (also referred to as NOx sensitivity). In the present embodiment, an Au content of the bottom electrode portion 22b is set to be 0.3 wt % or more smaller than that of the ceiling electrode portion 22a, because the bottom electrode portion 22b is closer to the heater part 70 than the ceiling electrode portion 22a to have a relatively high temperature when the gas sensor 100 is in use, and to thereby be likely to cause evaporation of Au. Decomposition of NOx and reduction in NOx sensitivity caused by evaporation of Au with continuous use are thus suppressed.

In a case where these requirements (a) to (c) are satisfied, decomposition of NOx and reduction in NOx sensitivity are suitably suppressed even if, by continuous use of the gas sensor 100, the inner pump electrode 22 is continuously exposed to a high temperature atmosphere for a long time to cause evaporation of Au from the inner pump electrode 22. As the size of the conducting portion is virtually negligible, the total area of the ceiling electrode portion 22a and the bottom electrode portion 22b shown in the requirement (c) can be considered as the total area of the inner pump electrode 22.

In the present embodiment, however, a change in NOx sensitivity is evaluated by the magnitude of a change rate of a slope shown by the sensitivity characteristics before and after an accelerated durability test in which the gas sensor 100 is installed onto an exhaust pipe of a diesel engine, and exposed to an exhaust gas for 3000 hours.

Specifically, a ratio (percentage) of a value of a difference in slope of the sensitivity characteristics before and after the accelerated durability test to the magnitude of the slope before the accelerated durability test is set to a NOx sensitivity change rate, and, when a value of the NOx sensitivity change rate is 20% or less, it is determined that the change in NOx sensitivity is in an allowable range (e.g., in a range in which measurement accuracy can be secured by correction of the sensitivity characteristics).

The gas sensor 100 satisfying the above-mentioned requirements (a) to (c) satisfies the requirement of the NOx sensitivity change rate of 20% or less.

In particular, when the NOx sensitivity change rate is 10% or less, it is determined that the change in NOx sensitivity is suitably suppressed.

The requirement of the NOx sensitivity change rate of 10% or less is satisfied in a case where the gas sensor 100 satisfying the above-mentioned requirements (a) to (c) further satisfies the following requirements (d) and (e):

(d) The ceiling electrode portion 22a has an Au content with respect to the Au—Pt alloy as a whole of 0.8 wt % to 3.0 wt %; and (e) The bottom electrode portion 22b has an Au content with respect to the Au—Pt alloy as a whole of 0 wt % to 0.6 wt %.

Decomposition of NOx in the main pump cell 21 in a case where the gas sensor 100 is in continuous use is more likely to be caused when the measurement gas introduced into the first internal space 20 has a higher oxygen concentration. This is because, as the oxygen concentration increases, the main pump voltage Vp0 increases, and NOx becomes more likely to be decomposed. It is thus possible to determine whether decomposition of NOx is caused by seeing dependency of the NOx current Ip2 on the oxygen concentration when the oxygen concentration is changed in an atmosphere having a constant NOx concentration. A degree of evaporation of Au can also be determined based on the dependency because such decomposition of NOx is more significantly likely to be caused in a case where evaporation of Au as described above is caused.

FIG. 2 is a plot of NOx currents Ip2 against the oxygen concentrations of model gases in order to show such dependency of the NOx current Ip2 on the oxygen concentration of the measurement gas, in which the NOx currents Ip2 are obtained through measurement (hereinafter, referred to as model gas measurement) targeted at four model gases having different oxygen concentrations of 0%, 5%, 10%, and 18% while having a constant NO concentration of 500 ppm (the balance being $N_2$ in each of the model gases) using two gas sensors 100 in different states. The sensor element driving temperature was 850° C.

Specifically, a graph G1 is a plot of results of measurement using a new gas sensor 100, and a graph G2 is a plot of results of measurement using a gas sensor 100 obtained by placing a new sensor element 101 in air, and conducting a continuous operation test for 3000 hours at the above-mentioned element driving temperature. The continuous operation test is positioned as a (an accelerated) durability test to evaluate a degree of deterioration over time. The term "new" does not necessarily mean "completely unused". Use for about several hours is accepted.

As shown in FIG. 2, in the graph G1, there is a linear change of a monotonous increase between the NOx current Ip2 and the oxygen concentration. A determination coefficient (a value of the square of a correlation coefficient) $R^2$ as obtained was 0.999, which indicates a substantially straight line. In the other graph G2, a value of the NOx current Ip2 is generally smaller than that in the graph G1, and levels off when the oxygen concentration is between 10% and 18% while having a tendency to monotonously increase when the oxygen concentration is 10% or less.

The results suggest that, in the gas sensor 100 having been used for a long time or continuously, a measurement value of the NOx current Ip2 is smaller than that in the new gas sensor 100, and furthermore, in a case where the measurement gas has a high oxygen concentration, NOx in the measurement gas tends to be decomposed at a stage before reaching the measurement electrode 44 (e.g., in the first internal space 20).

In light of reduction in linearity on a high oxygen concentration side as a result of decomposition of NOx, in the present embodiment, the determination coefficient $R^2$ obtained from the results of the above-mentioned model gas measurement is used as an indicator of stability of a pumping ability in the main pump cell 21 with respect to a change in oxygen concentration.

In the present embodiment, even in a case where the measurement gas has a high oxygen concentration, decomposition of NOx in the measurement gas at the stage before NOx reaches the measurement electrode 44 is suitably suppressed by satisfying the requirements (a) to (c). That is to say, in a case where model gas measurement as described above is performed, a monotonous increase as in the graph G1 or a similar graph is obtained, and leveling off of the value of the NOx current Ip2 in the high oxygen concentration range as in the graph G2 is not caused.

Specifically, a value of the determination coefficient $R^2$ obtained though model gas measurement performed after the above-mentioned accelerated durability test falls within a range of 0.950 or more or preferably within a range of 0.975 or more.

In a case where the bottom electrode portion 22b has an Au content of 0 wt % in the requirement (e), decomposition of NOx in the bottom electrode portion 22b is easily caused as the effect obtained by containing Au cannot be obtained, but it has been confirmed by the inventors of the present invention that the influence therefrom on the NOx sensitivity and the determination coefficient is within an allowable range as long as the other requirements are satisfied.

The graph G1 in FIG. 2 shows that the value of the NOx current Ip2 tends to depend on the oxygen concentration of the measurement gas. This suggests that, in determining the NOx concentration based on the sensitivity characteristics, correction using the oxygen concentration is effective to determine the NOx concentration with more accuracy. This can be achieved, for example, by correcting the NOx current Ip2 based on information (e.g., the main pump current Ip0 and the electromotive force Vref) indicating the oxygen concentration of the measurement gas.

<Process of Manufacturing Sensor Element>

A process of manufacturing the sensor element 101 having a configuration and features as described above will be described next. In the present embodiment, a laminated body of green sheets containing an oxygen-ion conductive solid electrolyte, such as zirconia, as a ceramic component is formed, and cut and fired to manufacture the sensor element 101.

Figure 3:
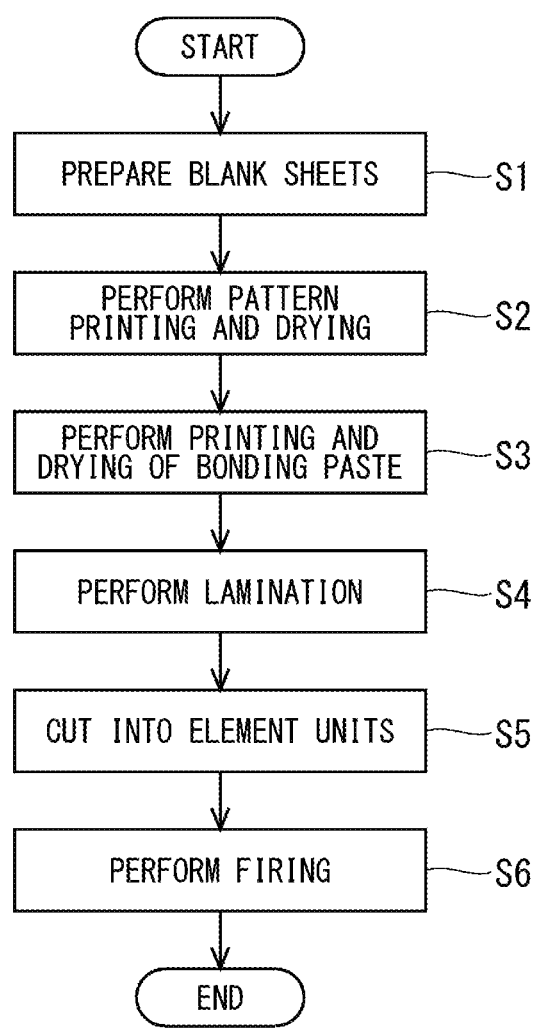
FIG. 3 shows a flow of processing performed when the sensor element 101 is manufactured.

A case where the sensor element 101 including the six layers illustrated in FIG. 1 is manufactured will be described as an example below. In this case, six green sheets corresponding to the first substrate layer 1, the second substrate layer 2, the third substrate layer 3, the first solid electrolyte layer 4, the spacer layer 5, and the second solid electrolyte layer 6 are to be prepared. FIG. 3 shows a flow of processing when the sensor element 101 is manufactured.

In a case where the sensor element 101 is manufactured, blank sheets (not illustrated) being green sheets having no pattern formed thereon are prepared first (step S1). In a case where the sensor element 101 including the six layers is manufactured, six blank sheets are prepared to correspond to the respective layers. In particular, as a green sheet to be the second solid electrolyte layer 6, a green sheet having a thickness to eventually enable the requirement (d) and further the requirement (b) to be satisfied is used.

The blank sheets have a plurality of sheet holes used for positioning in printing and lamination. The sheet holes are formed to the blank sheets in advance prior to pattern formation through, for example, punching by a punching machine. Green sheets corresponding to layers constituting an internal space also include penetrating portions corresponding to the internal space formed in advance through, for example, punching as described above. The blank sheets corresponding to the respective layers of the sensor element 101 are not required to have the same thickness.

When the blank sheets corresponding to the respective layers are prepared, pattern printing and drying are performed on the individual blank sheets (step S2). Specifically, a pattern of various electrodes, a pattern of the fourth diffusion control part 45, a pattern of the heater element 72 and the heater insulating layer 74, a pattern of internal wiring, which is not illustrated, and the like are formed. Application or placement of a sublimable material for forming the first diffusion control part 11, the second diffusion control part 13, and the third diffusion control part 30 is also performed at the time of pattern printing.

The patterns are printed by applying pastes for pattern formation prepared in accordance with characteristics required for respective formation targets onto the blank sheets using known screen printing technology. A known drying means can be used for drying after printing.

In particular, in forming a pattern of the inner pump electrode 22, a paste for formation of the ceiling electrode portion 22a and a paste for formation of the bottom electrode portion 22b are prepared so that the inner pump electrode 22 in an eventually formed state satisfies the above-mentioned requirements (a) and (b) and further the requirements (d) and (e). Each of the pastes is applied at a predetermined location so that the inner pump electrode 22 as eventually formed satisfied the above-mentioned requirement (c).

When pattern printing on each of the blank sheets ends, printing and drying of a bonding paste are performed to laminate and bond the green sheets corresponding to the respective layers (step S3). The known screen printing technology can be used for printing of the bonding paste, and the known drying means can be used for drying after printing.

The green sheets to which the bonding agent has been applied are then stacked in a predetermined order, and the stacked green sheets are crimped under a predetermined temperature and pressure condition to thereby form a laminated body (step S4). Specifically, crimping is performed by stacking and holding the green sheets as a target of lamination on a predetermined lamination jig, which is not illustrated, while positioning the green sheets at the sheet holes, and then heating and pressurizing the green sheets together with the lamination jig using a lamination machine, such as a known hydraulic pressing machine. The pressure, temperature, and time for heating and pressurizing depend on a lamination machine to be used, and an appropriate condition is determined to achieve good lamination.

When the laminated body is obtained as described above, the laminated body is then cut at a plurality of locations into units (referred to as element bodies) to become individual sensor elements 101 (step S5).

The cut element bodies are each fired at a firing temperature of approximately 1300° C. to 1500° C. (step S6). The sensor element 101 is thereby manufactured. That is to say, the sensor element 101 is generated through integral firing of the solid electrolyte layers and the electrodes. The firing temperature in this case is preferably 1200° C. or more and 1500° C. or less (e.g., 1400° C.). Integral firing is performed in this manner, so that the electrodes each have sufficient adhesion strength in the sensor element 101.

The sensor element 101 thus obtained is housed in a predetermined housing, and built into the body (not illustrated) of the gas sensor 100.

As described above, in the present embodiment, the inner pump electrode as the cermet electrode of the Pt—Au alloy and $ZrO_2$ provided to face the internal space in the sensor element of the gas sensor and forming the main pump cell to pump out oxygen from the internal space is provided so that the ceiling electrode portion farther from the heater part and the bottom electrode portion closer to the heater part satisfy the above-mentioned requirements (a) to (c) to suppress the influence of evaporation of Au from the inner pump electrode caused by continuous use on the NOx sensitivity. Furthermore, decomposition of NOx in the internal space in a case where the oxygen concentration is high is suppressed.

<Modification>

In the above-mentioned embodiment, the measurement electrode 44 is placed in the second internal space 40 to be covered with the fourth diffusion control part 45 functioning as the porous protective film and providing the predetermined diffusion resistance to the measurement gas, and the amount of NOx flowing into the measurement electrode 44 is limited by the fourth diffusion control part 45. Alternatively, however, a third internal space communicating with the second internal space 40, for example, through a slit-like or porous diffusion control part providing, to the measurement gas, diffusion resistance equivalent to the diffusion resistance provided by the fourth diffusion control part 45 may be provided, and the measurement electrode 44 may be provided in the third internal space.

Figure 4:
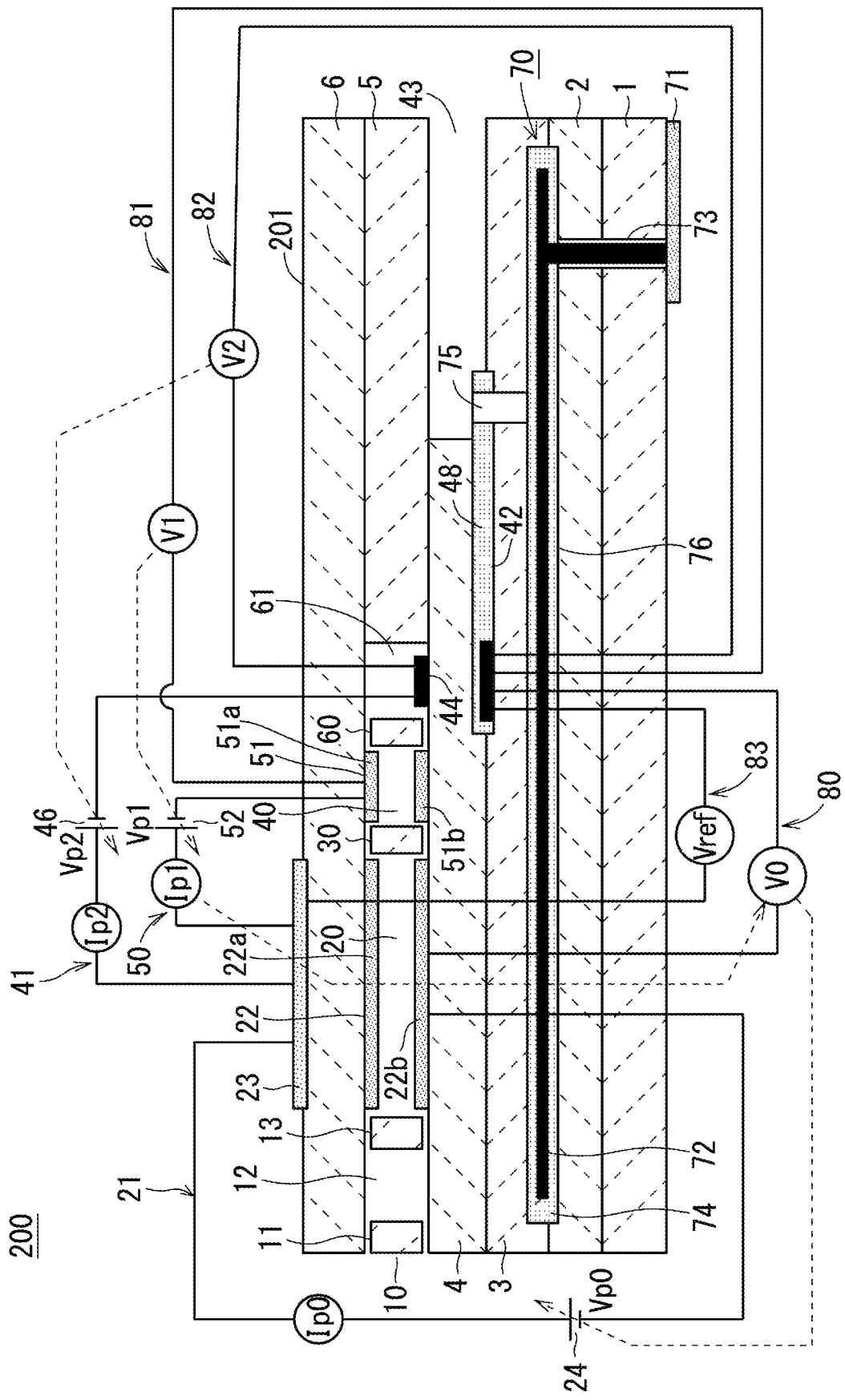
FIG. 4 schematically shows one example of a configuration of a gas sensor 200.

FIG. 4 schematically shows one example of a configuration of a gas sensor 200 including a vertical sectional view taken along a longitudinal direction of a sensor element 201 having such a configuration. The sensor element 201 includes common components in action and functions with the components of the sensor element 101 illustrated in FIG. 1. Such components bear the same reference signs as those of the corresponding components illustrated in FIG. 1, and detailed description thereof is omitted unless it is necessary. The controller 110 is not illustrated.

The sensor element 201 is different from the sensor element 101 illustrated in FIG. 1 in that the first diffusion control part 11 doubles as the gas inlet 10, a third internal space 61 communicating with the second internal space 40 through a slit-like fifth diffusion control part 60 similar to the first diffusion control part 11, the second diffusion control part 13, and the third diffusion control part 30 is provided, the measurement electrode 44 is provided on an upper surface of a portion of the first solid electrolyte layer 4 facing the third internal space 61, and the measurement electrode 44 is exposed to the third internal space 61. The sensor element 201, however, is similar to the sensor element 101 in that a diffusion control part is located between the second internal space 40 and the measurement electrode 44.

In the sensor element 201, the influence of evaporation of Au from the inner pump electrode 22 caused by continuous use on the NOx sensitivity is suppressed and decomposition of NOx in the first internal space 20 in a case where the oxygen concentration is high is suppressed by satisfying the requirements (a) to (c).

EXAMPLES

Thirteen types of gas sensors 100 having different combinations of Au contents and the total area of the ceiling electrode portion 22a and the bottom electrode portion 22b of the inner pump electrode 22 were manufactured. The accelerated durability test was conducted on each of the gas sensors 100, and the NOx sensitivity change rate and dependency of the NOx current on the oxygen concentration after the accelerated durability test were evaluated.

More particularly, as examples, nine types of gas sensors 100 (Examples 1 to 9) each satisfying all the above-mentioned requirements (a) to (c) concerning the inner pump electrode 22 were manufactured, and, as comparative examples, four types of gas sensors 100 (Comparative Examples 1 to 4) each not satisfying at least one of the requirements (a) to (c) were manufactured. In particular, the gas sensors 100 of Examples 1 to 4 and 6 each also satisfied the requirements (d) and (e).

Examples 1 to 6 and Comparative Examples 1 and 2 were different in Au contents of the ceiling electrode portion 22a and the bottom electrode portion 22b while having a constant total area of the inner pump electrode, and Examples 5 and 7 to 9 and Comparative Examples 3 and 4 were different in total area of the inner pump electrode while having constant Au contents of and a constant difference in content between the ceiling electrode portion 22a and the bottom electrode portion 22b. In each of the gas sensors 100, the ceiling electrode portion 22a and the bottom electrode portion 22b had a thickness of 15 μm.

The accelerated durability test was conducted under a condition below: Each of the gas sensors 100 was installed onto an exhaust pipe of an engine, and a 40-minute driving pattern configured to have an engine speed in a range of 1500 rpm to 3500 rpm and a load torque in a range of 0 N·m to 350 N·m was repeated until 3000 hours had elapsed. In this case, temperature of the gas was maintained within a range of 200° C. to 600° C., and the NOx concentration was set to have a value within a range of 0 ppm to 1500 ppm.

The NOx current Ip2 was measured using model gases before the start, at 1000 hours after the start, at 2000 hours after the start, and at the end (at 3000 hours after the start) of the accelerated durability test.

The model gas measurement was performed using four model gases having different oxygen concentrations of 0%, 5%, 10%, and 18% while having a constant NO concentration of 500 ppm (the balance being $N_2$ in each of the model gases). The element driving temperature was set to 850° C. in each case.

Then, a value as a slope of the sensitivity characteristics (a change rate of the NOx current to a value of the NO concentration) was calculated by dividing a measurement value of the NOx current Ip2 at the respective oxygen concentration by the NO concentration (500 ppm) in a case where the oxygen concentration is 0%, at each of the above-mentioned time points, and further, the NOx sensitivity change rate being a change rate of the slope at each elapsed time was calculated using, as a reference (an initial value), the slope of the sensitivity characteristics before the start of the accelerated durability test, and, based on a value thereof, a degree of a change in NOx sensitivity of each of the gas sensors 100 was determined.

FIG. 5 is a plot of NOx sensitivity change rates of the gas sensors of Examples 1 to 5 and Comparative Examples 1 and 2 against the elapsed times of the accelerated durability test. It can be seen from FIG. 5 that, while (the absolute value of) the NOx sensitivity change rate of each of the gas sensors monotonously changes with elapsed time of the accelerated durability test, (the absolute value of) the NOx sensitivity change rate of each of the gas sensors of Examples 1 to 5 is limited to 15% or less even after the elapse of 3000 hours, whereas (the absolute value of) the NOx sensitivity change rate of each of the gas sensors of Comparative Examples 1 and 2 exceeds 20%.

The determination coefficient $R^2$ as an indicator of dependency of the NOx current Ip2 on the oxygen concentration as shown in FIG. 2 was calculated from results of the model gas measurement at the end of the accelerated durability test, and, based on a value thereof, a degree of decomposition of NOx in the inner pump electrode 22 was determined.

The Au content of the ceiling electrode portion 22a, the Au content of the bottom electrode portion 22b, a difference in content between them, the total area of the inner pump electrode 22, a result of determination on whether the NOx sensitivity change rate is preferable (DETERMINATION 1), and a result of determination on whether the determination coefficient $R^2$ is preferable (DETERMINATION 2) of each of the gas sensors of Examples 1 to 9 and Comparative Examples 1 to 4 are shown in Table 1 as a list.

TABLE 1

| | Au CONTENT OF INNER PUMP ELECTRODE (wt %) | | DIFFERENCE IN CONTENT | TOTAL AREA OF INNER PUMP ELECTRODE | | |
|---|---|---|---|---|---|---|
| | CEILING | BOTTOM | (wt %) | (mm²) | DETERMINATION 1 | DETERMINATION 2 |
| EXAMPLE 1 | 1.1 | 0.6 | 0.5 | 15 | ○ | ○ |
| EXAMPLE 2 | 1.2 | 0.0 | 1.2 | 15 | ○ | ○ |
| EXAMPLE 3 | 0.8 | 0.3 | 0.5 | 15 | ○ | ○ |
| EXAMPLE 4 | 0.8 | 0.0 | 0.8 | 15 | ○ | ○ |
| EXAMPLE 5 | 1.0 | 0.7 | 0.3 | 15 | Δ | Δ |
| EXAMPLE 6 | 3.0 | 0.5 | 2.5 | 15 | ○ | ○ |
| COMPARATIVE EXAMPLE 1 | 1.0 | 1.0 | 0 | 15 | x | Δ |
| COMPARATIVE EXAMPLE 2 | 1.0 | 0.8 | 0.2 | 15 | x | Δ |
| EXAMPLE 7 | 1.0 | 0.7 | 0.3 | 25 | Δ | ○ |
| EXAMPLE 8 | 1.0 | 0.7 | 0.3 | 20 | Δ | ○ |
| EXAMPLE 9 | 1.0 | 0.7 | 0.3 | 10 | ○ | Δ |
| COMPARATIVE EXAMPLE 3 | 1.0 | 0.7 | 0.3 | 8 | ○ | x |
| COMPARATIVE EXAMPLE 4 | 1.0 | 0.7 | 0.3 | 9 | ○ | x |

In determination on the degree of the change in NOx sensitivity of each of the gas sensors 100 shown as DETERMINATION 1, in a case where (the absolute value of) the NOx sensitivity change rate is 10% or less, it is determined that the change in NOx sensitivity is suitably suppressed, and a circle is marked in Table 1.

In a case where (the absolute value of) the NOx sensitivity change rate is more than 10% and 20% or less, it is determined that the change in NOx sensitivity is suppressed within a range allowable in actual use of each of the gas sensors 100, and a triangle is marked in Table 1.

On the other hand, as for each of the gas sensors 100 having a NOx sensitivity change rate of more than 20% and thus not corresponding to any of the above-mentioned cases, a cross is marked.

On the other hand, in determination on the degree of decomposition of NOx shown as DETERMINATION 2, in a case where the value of the determination coefficient $R^2$ is 0.975 or more, it is determined that decomposition of NOx is suitably suppressed, and a circle is marked in Table 1.

In a case where the value of the determination coefficient $R^2$ is 0.950 or more and less than 0.975, it is determined that decomposition of NOx is suppressed within a range allowable in actual use of each of the gas sensors 100, and a triangle is marked in Table 1.

On the other hand, as for each of the gas sensors 100 having a value of the determination coefficient $R^2$ of less than 0.950 and thus not corresponding to any of the above-mentioned cases, a cross is marked.

In Table 1, the circle or the triangle is marked in both of DETERMINATION 1 and DETERMINATION 2 for each of the gas sensors 100 of Examples 1 to 9 satisfying all the requirements (a) to (c). This indicates that, in each of the gas sensors 100 of these examples, the change in NOx sensitivity and decomposition of NOx are each suppressed within the range allowable in actual use.

In contrast, in cases of Comparative Examples 1 and 2, the change in NOx sensitivity is significant beyond the allowable range as can be seen from the cross marked in DETERMINATION 1 and FIG. 5. In cases of Comparative Examples 3 and 4, decomposition of NOx in the inner pump electrode 22 in a case where the oxygen concentration is high is significantly caused as can be seen from the cross marked in DETERMINATION 2.

It is confirmed from the results that all the requirements (a) to (c) are required to be satisfied to suppress the change in NOx sensitivity and decomposition of NOx when the gas sensor 100 is in continuous use.

In particular, the circle is marked in both of DETERMINATION 1 and DETERMINATION 2 for each of the gas sensors 100 of Examples 1 to 4 and 6 also satisfying the requirements (d) and (e). This means that the change in NOx sensitivity and decomposition of NOx are each suitably suppressed.

It is confirmed from the results that, in a case where the requirements (d) and (e) are satisfied in addition to the requirements (a) to (c), the change in NOx sensitivity and decomposition of NOx when the gas sensor 100 is in continuous use are suitably suppressed.

While the invention has been shown and described in detail, the foregoing description is in all aspects illustrative and not restrictive. It is therefore understood that numerous modifications and variations can be devised without departing from the scope of the invention.

What is claimed is:

1. A sensor element for a limiting-current type gas sensor measuring concentration of NOx in a measurement gas, said sensor element comprising:
    a base part made of an oxygen-ion conductive solid electrolyte;
    a gas inlet through which said measurement gas is introduced from an external space;
    a first internal space communicating with said gas inlet under predetermined diffusion resistance;
    a main pump cell as an electrochemical pump cell including an inner pump electrode located to face said first internal space, an out-of-space pump electrode located to face a space other than said first internal space, and said solid electrolyte located between said inner pump electrode and said out-of-space pump electrode;
    a measurement electrode located inside said sensor element, at least one diffusion control part being located between said measurement electrode and said first internal space;
    a reference electrode located inside said sensor element and capable of being in contact with a reference gas;
    a measurement pump cell as an electrochemical pump cell including said measurement electrode, said out-of-space pump electrode, and said solid electrolyte located between said measurement electrode and said out-of-space pump electrode; and
    a heater part buried in said sensor element and heating said sensor element, wherein
    said inner pump electrode is at least made of a cermet of a Pt—Au alloy and zirconia, and includes:
        a first portion located on a surface farther from said heater part from among surfaces opposing each other in said first internal space; and
        a second portion located on a surface closer to said heater part from among said surfaces opposing each other in said first internal space,
    an Au content with respect to said Pt—Au alloy as a whole of said second portion is 0.3 wt % or more smaller than an Au content with respect to said Pt—Au alloy as a whole of said first portion, and
    a total area of said first portion and said second portion is 10 mm$^2$ to 25 mm$^2$.

2. The sensor element according to claim 1, wherein
    said first portion has an Au content with respect to said Pt—Au alloy as a whole of 0.8 wt % to 3.0 wt %, and
    said second portion has an Au content with respect to said Pt—Au alloy as a whole of 0 wt % to 0.6 wt %.

3. The sensor element according to claim 2, further comprising:
    a second internal space communicating with said first internal space under predetermined diffusion resistance; and
    an auxiliary pump cell as an electrochemical pump cell including an auxiliary pump electrode located to face said second internal space, said out-of-space pump electrode, and said solid electrolyte located between said auxiliary pump electrode and said out-of-space pump electrode, wherein
    a diffusion control part is at least located between said measurement electrode and said second internal space.

4. The sensor element according to claim 1, further comprising:
    a second internal space communicating with said first internal space under predetermined diffusion resistance; and
    an auxiliary pump cell as an electrochemical pump cell including an auxiliary pump electrode located to face said second internal space, said out-of-space pump electrode, and said solid electrolyte located between said auxiliary pump electrode and said out-of-space pump electrode, wherein
    a diffusion control part is at least located between said measurement electrode and said second internal space.

* * * * *